United States Patent [19]

Lau

[11] Patent Number: 4,990,436

[45] Date of Patent: Feb. 5, 1991

[54] CYAN DYE-FORMING COUPLERS AND PHOTOGRAPHIC RECORDING MATERIALS CONTAINING SAME

[75] Inventor: Philip T. S. Lau, Rochester, N.Y.

[73] Assignee: Eastman Kodak Company, Rochester, N.Y.

[21] Appl. No.: 469,008

[22] Filed: Jan. 23, 1990

[51] Int. Cl.$^5$ .............................................. G03C 7/34
[52] U.S. Cl. ................................... 430/552; 430/553; 430/558
[58] Field of Search ................... 430/552, , 553, 558, 430/384, 385

[56] References Cited

U.S. PATENT DOCUMENTS

| | | | |
|---|---|---|---|
| 2,313,138 | 3/1943 | Frolich et al. | 430/552 |
| 2,369,929 | 2/1945 | Vittum et al. | 430/552 |
| 2,525,502 | 10/1950 | Tulagin et al. | 430/558 |
| 2,717,831 | 9/1955 | Tulagin et al. | 430/558 |
| 4,333,999 | 6/1982 | Lau | 430/553 |

FOREIGN PATENT DOCUMENTS 1210954  8/1989  Japan ................... 430/553

Primary Examiner—Paul R. Michl
Assistant Examiner—Lee C. Wright
Attorney, Agent, or Firm—Richard E. Knapp

[57] ABSTRACT

Tetrahydroquinoline rings fused to a phenolic ring form novel cyan due-forming coupler compounds which produce dyes having improved resistance to ferrous ion reduction.

Photographic recording materials containing such coupler compounds are also disclosed.

10 Claims, No Drawings

CYAN DYE-FORMING COUPLERS AND PHOTOGRAPHIC RECORDING MATERIALS CONTAINING SAME

The present invention relates to novel cyan dye-forming coupler compounds and to photographic recording materials containing such compounds.

Couplers which are used to obtain cyan dyes are typically phenols and naphthols. Such couplers yield azomethine dyes upon coupling with oxidized primary amino color developing agents. U.S. Pat. No. 4,333,999 describes, for example, ballasted phenolic cyan dye-forming couplers which comprise a cyanophenylureido group in the 2-position of the phenolic ring. This particular class of couplers has found wide commercial acceptance in photographic applications. Included among the important advantages of these couplers is their ability to provide cyan dyes of high purity with hue values which are shifted bathochromically to the long wavelength red absorption region. This latter property provides dyes in which unwanted green light absorption is minimized.

U.S. Pat. No. 2,369,929 describes 2,5-disubstituted phenolic compounds which are capable of producing cyan dyes when reacted with oxidized primary aromatic amino developing agents.

U.S. Pat. No. 2,313,138 describes substituted naphtholic compounds which are capable of yielding cyan dyes when reacted with oxidized primary amine developing agents.

However, one of the problems with the known cyan dyes formed from these couplers is their lack of ferrous ion stability. This shortcoming is observed in the form of dye color loss which occurs in the bleaching step of a color development process.

Accordingly, there is a need to provide cyan dye forming coupler compounds which yield dyes having improved stability to ferrous ion.

The present invention is based upon the provision of a new class of cyan coupler compounds which comprise a tetrahydroquinoline ring fused to a phenolic ring which have the following structural formula:

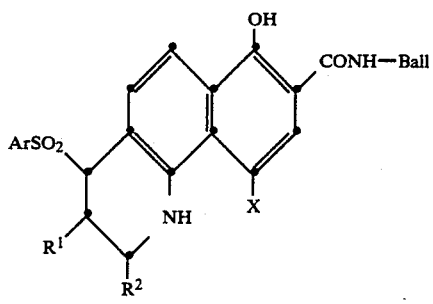

wherein:
Ar is an aryl group having from 6 to about 10 carbon atoms which may be substituted;
R¹ and R², which may be the same or different, represent hydrogen or an alkyl group having from 1 to about 20 carbon atoms;
Ball is an organic ballasting group capable of rendering the coupler compound non-diffusible during development in alkaline processing solution; and
X is hydrogen or a coupling off group.

The present invention also provides a photographic recording material which comprises a support and a photosensitive silver halide emulsion which has associated therewith a cyan dye-forming coupler compound having the structural formula:

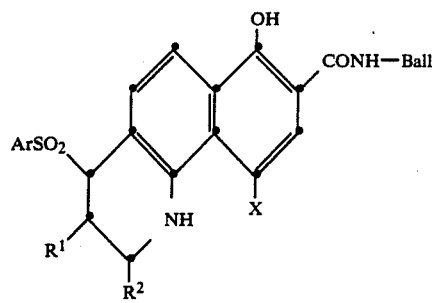

wherein:
Ar is an aryl group having from 6 to about 10 carbon atoms which may be substituted;
$R^1$ and $R^2$, which may be the same or different, represent hydrogen or an alkyl group having from 1 to about 20 carbon atoms;
Ball is an organic ballasting group capable of rendering the coupler compound non-diffusible during development in alkaline processing solution; and
X is hydrogen or a coupling-off group.

In the coupler compounds of the present invention, Ar is a phenyl or a naphthyl group. Substituents may be present on these groups so long the chosen substituent does not have any adverse effect upon the activity of the dye-forming coupler compounds. The types of substituents include alkyl or alkoxy groups having from 1 to about 30 carbon atoms, sulfonamido groups having the formula $-NHSO_2R^3$ and carbonamido groups having he formula $-NHCOR^3$ where $R^3$ is alkyl of from 1 to about 30 carbon atoms or aryl having from 6 to about 20 carbon atoms.

A preferred Ar group is unsubstituted or substituted phenyl where the substituent comprises an alkyl group having from 1 to about 16 carbon atoms.

While the $R^1$ and $R^2$ groups comprise from 1 to about 20 carbon atoms, preferred alkyl groups have from 1 to about 10 carbon atoms. Especially preferred coupler compounds are those where $R^1$ is hydrogen and $R^2$ is methyl.

Coupling-off groups represented by X are well known in the art. Such groups can determine the equivalency of the coupler, i.e., whether it is a 2-equivalent or a 4-equivalent coupler, or modify the reactivity of the coupler. Such groups can advantageously affect the layer in which the coupler is coated, or other layers in the photographic recording material, by performing, after release from the coupler, functions such as development inhibition, bleach inhibition, bleach acceleration, color correction and the like.

Representative classes of coupling-off groups include chloro, alkoxy, aryloxy, heteroyloxy, sulfonyloxy, acyloxy, acyl, heterocyclyl, sulfonamido, mercaptotetrazole, mercaptopropionic acid, phosphonyloxy and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U.K. Patents and published applications Nos. 1,466,728, 1,531,927, 1,533,039, 2,006,755A and 2,017,704A, the disclosures of which are incorporated herein by reference.

Examples of preferred coupling-off groups which can be represented by X are: H, Cl, F, —OCH$_3$, —OCH$_2$CONHCH$_2$CH$_2$OH, —OCH$_2$CONHCH$_2$CH$_2$OCH$_3$

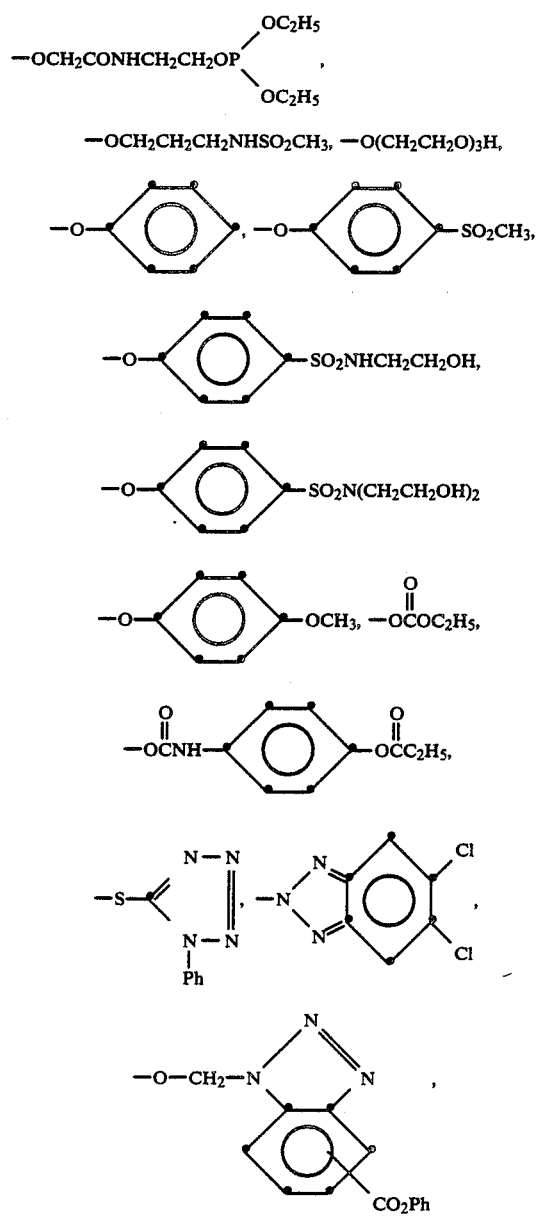

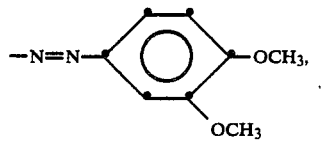

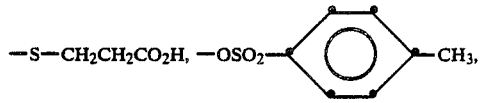

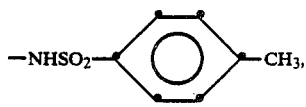

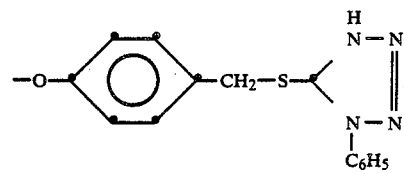

Representative BALL (ballast) groups are of such size and configuration as to confer on the coupler molecule sufficient bulk to render the coupler substantially non-diffusible from the layer in which it is coated in the described photographic recording material.

Representative ballast groups include substituted or unsubstituted alkyl or aryl groups containing 8 to 40 carbon atoms.

Representative substituents on such groups include alkyl, aryl, alkoxy, aryloxy, alkylthio, hydroxy, halogen, alkoxycarbonyl, aryloxycarbonyl, carboxy, acyl, acyloxy, amino, anilino, carbonamido, carbamoyl, alkylsulfonyl, arylsulfonyl, sulfonamido, and sulfamyl groups wherein the substituents typically contain 1 to 40 carbon atoms. Such substituents can also be further substituted.

Specific coupler compounds of this invention are shown below in Table I:

TABLE I

A.
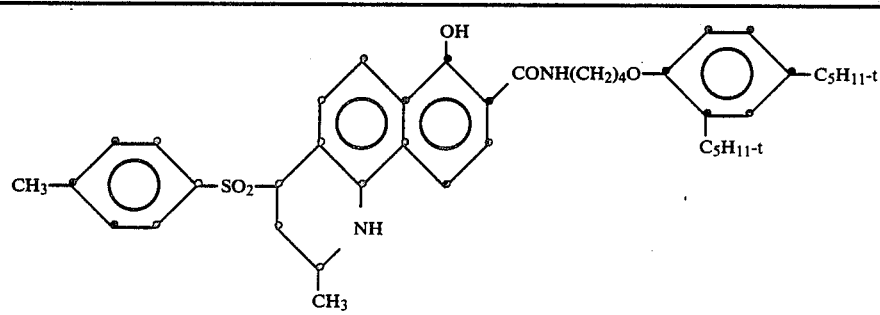

TABLE I-continued
B.
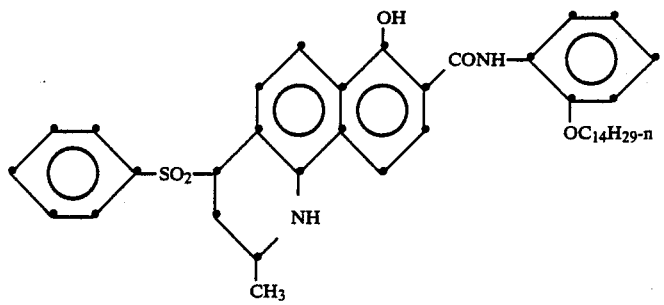
C.
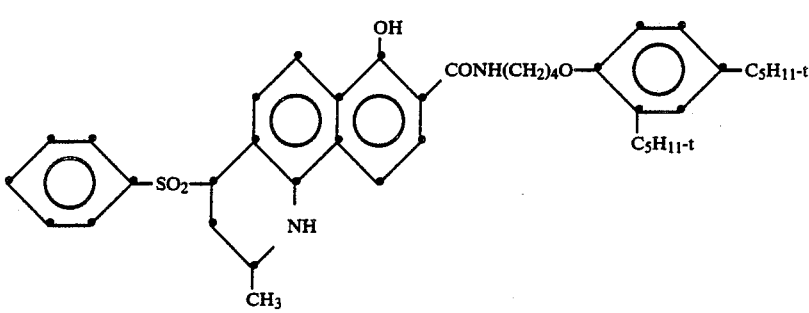
D.
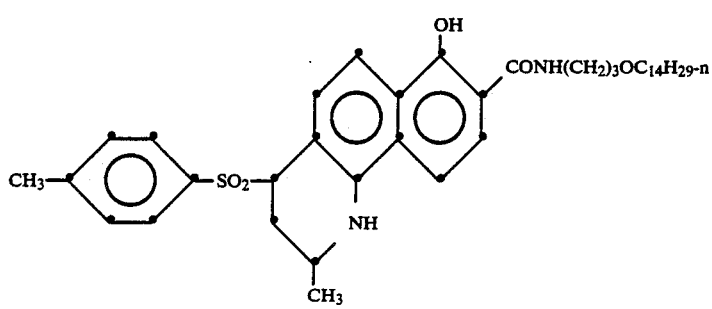
E.
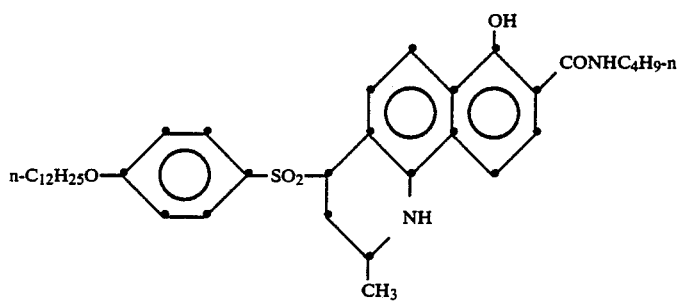
F.
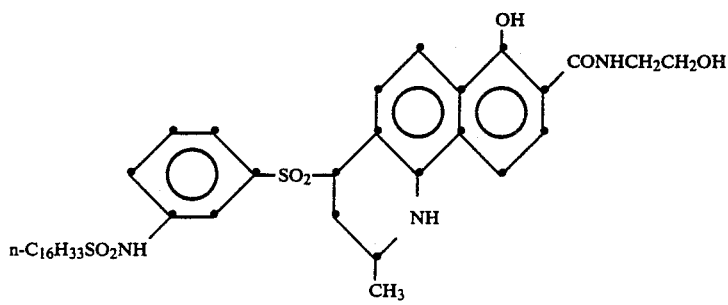

TABLE I-continued
G.
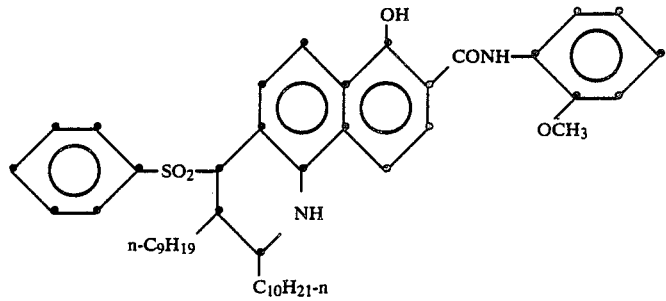
H.
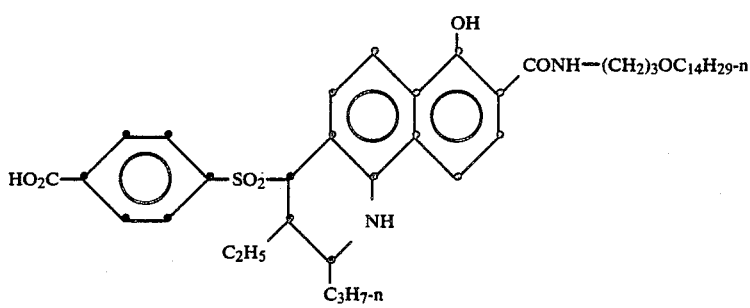
I.
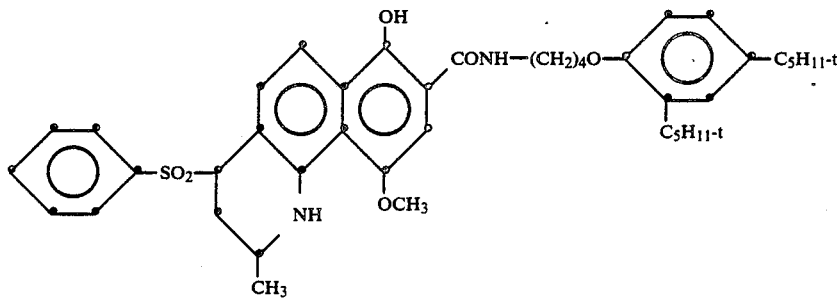
J.
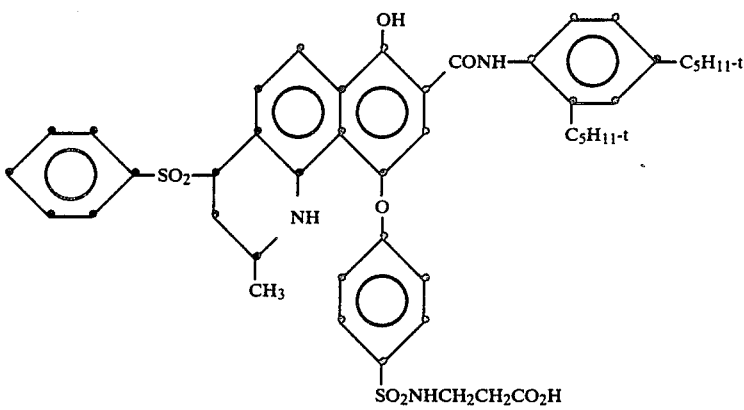
K.
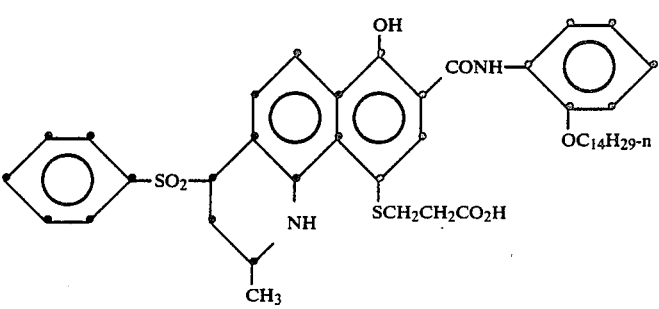

TABLE I-continued
L.
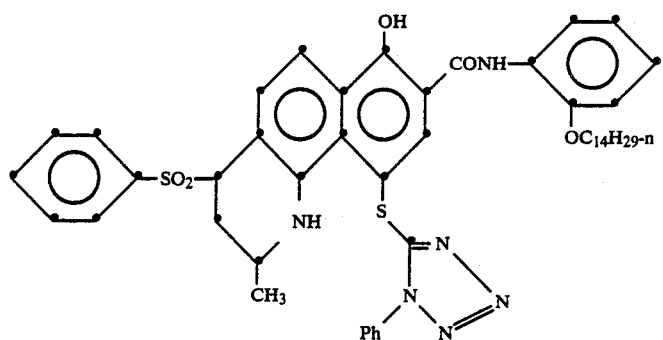
M.
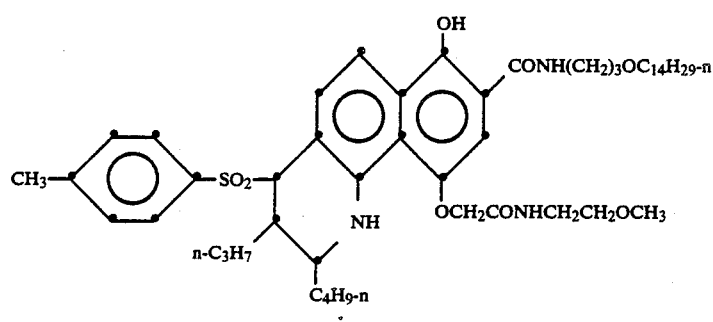
N.
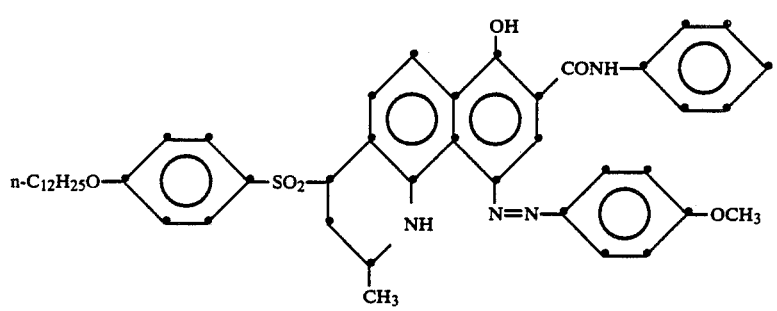
O.
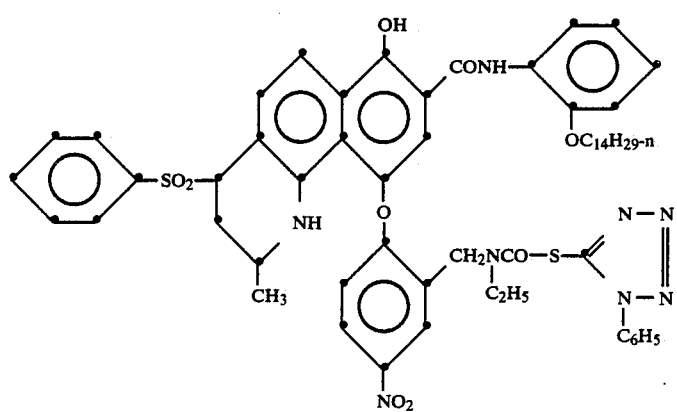

TABLE I-continued

P.

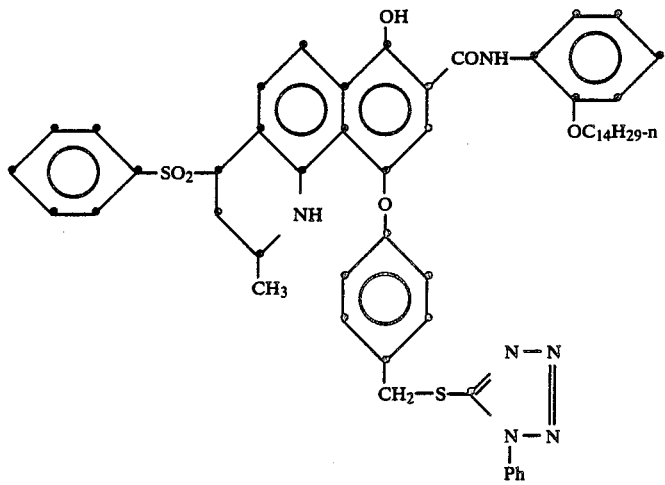

Coupler compounds of this invention are readily synthesized in high yields by reacting 1-hydroxy-5-amino-2-naphthoic acid with an enolizable aldehyde and an arylsulfinic acid according to the following scheme:

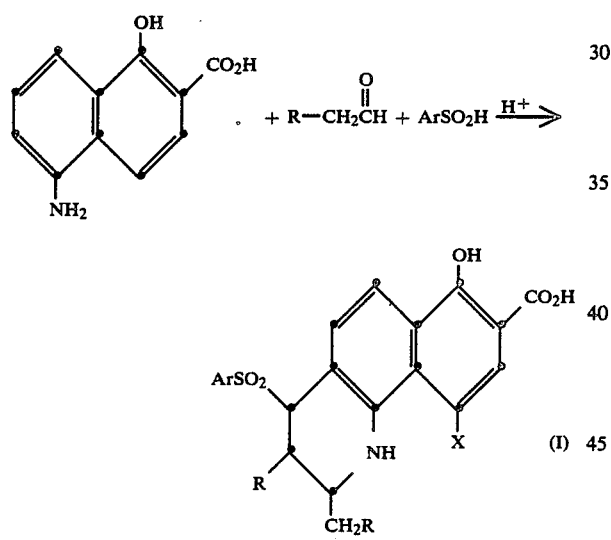

The carboxylic acid group in the 2-position of the naphthol is then reacted with an amino-ballast as follows:

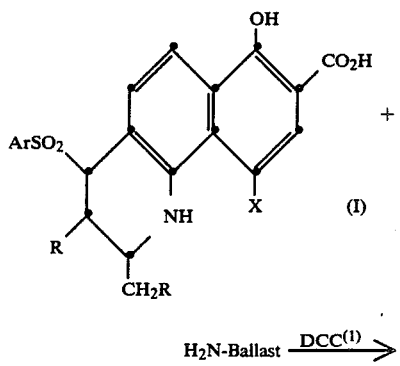

-continued

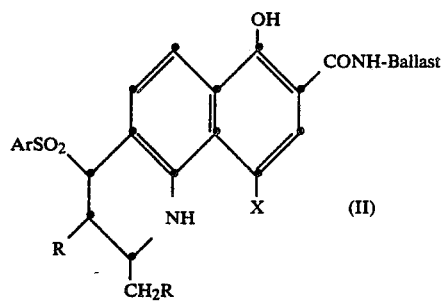

$^{(1)}$DCC = dicyclohexylcarbodiimide

The following preparations are specific illustrations of methods for synthesizing compounds described herein.

SYNTHESIS OF COUPLER COMPOUND A

To a suspension of 20.3 g (0.1 mole) of 2-carbonyl-5-aminonaphthol in 250 mL of ethanol was added with stirring 9.8 ml (0.1 mole) of concentrated HCl, 14.2 g (0.3 mole) of acetaldehyde and a solution of 21.4 g (0.1 mole) of sodium p-toluenesulfinate dissolved in 60 ml of water. Within 10 minutes of addition the suspended solid went into solution. The mixture was stirred at room temperature overnight. The yellow solid which precipitated out was collected and washed with boiling tetrahydrofuran to give 41.0 g (99.6%) of the pure product (I); m.p. 191°–192° C. The structure was consistent with its nmr spectrum.

Calcd. for $C_{22}H_{21}NO_5S$: C, 64.22; H, 5.14; N, 3.40; S, 7.79 Found: C, 64.37; H, 5.03; H, 3.41; S, 7.91.

To a suspension of 8.2 g (0.02 mole) of the product (I) prepared above in 150 ml tetrahydrofuran was added with stirring 6.1 g (0.02 mole) of 2,4-di-tert-amylphenoxybutylamine and 4.1 g (0.02 mole) of dicyclohexylcarbodiimide (DCC). The reaction mixture was stirred at room temperature overnight. The precipitated solid dicyclohexyl area was filtered off. The filtrate was drowned in ice water. A brown oil separated which solidified upon standing. The solid was collected, washed with water and ethanol. Recrystallized from tetrahydrofuran-ethylacetate to give 12.7 g (91%) of (II); m.p. 181°–182° C. The structure of the coupler is consistent with its NMR spectrum.

Calcd. for $C_{42}H_{54}H_2O_5S$: C,72.17; H,7.79; N,4.01; S,4.54. Found: C,72.01; H,7.84; H,4.11; S,4.54.

Other coupler compounds of this invention were prepared using analogous synthetic routes. Thus, coupler D is prepared using an equivalent amount of tetradecyloxypropanyl amine in place of 2,4-di-tert-amylphenoxybutyl amine; m.p. 156–157 C;

Calcd. for $C_{39}H_{56}N_2O_5S$: C,70.45; H,8.49; N,4.21; S,4.82 Found: C,70.37; H,8.48; N,4.50; S,4.14.

The couplers of this invention can be incorporated in silver halide emulsions and the emulsions can be coated on a support to form a photographic material. Alternatively, at least one of the couplers can be incorporated in photographic layers adjacent the silver halide emulsion layer where, during development, the coupler will be in reactive association with development products such as oxidized color developing agent.

The photographic recording materials can be either single color or multicolor. In a multicolor material, the yellow dye-forming coupler is usually associated with a blue-sensitive emulsion, although it could be associated with an unsensitized emulsion or an emulsion sensitized to a different region of the spectrum. Multicolor materials contain dye image-forming units sensitive to each of the three primary regions of the spectrum. Each unit can be comprised of a single emulsion layer or of multiple emulsion layers sensitive to a given region of the spectrum. These layers, including the layers of the image-forming units, can be arranged in various orders as known in the art.

A typical multicolor photographic recording material comprises a support bearing a cyan dye image-forming unit comprising at least one red-sensitive silver halide emulsion layer having associated therewith at least one cyan dye-forming coupler, a magenta image-forming unit comprising at least one green-sensitive silver halide emulsion layer having associated &herewith at least one magenta dye-forming coupler and a yellow dye image-forming unit comprising at least one blue-sensitive silver halide emulsion layer having associated therewith at least one yellow dye-forming coupler. The recording material can contain additional layers, such as filter layers, interlayers, overcoat layers, subbing layers, and the like.

In the following discussion of suitable materials for use in this invention, reference will be made to *Research Disclosure*. December 1978, Item 17643, published by Kenneth Mason Publications, Ltd., The Old Harbourmaster's, 8 North Street, Emsworth, Hampshire PO10 7DD, ENGLAND, the disclosures of which are incorporated herein by reference. This publication will be identified hereafter by the term *Research Disclosure*.

The silver halide emulsions employed in this invention can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al U.S. Pat. No. 4,434,226, Daubendiek et al U.S. Pat. No. 4,414,310, Wey U.S. Pat. No. 4,399,215, Solberg et al U.S Pat. No. 4,433,048, Mignot U.S. Pat. No. 4,386,156, Evans et al U.S. Pat. No. 4,504,570, Maskasky U.S. Pat. No. 4,400,463, Wey et al U.S. Pat. No. 4,414,306, Maskasky U.S. Pat Nos. 4,435,501 and 4,643,966 and Daubendiek et al U.S. Pat. Nos. 4,672,027 and 4,693,964. Also specifically contemplated are those silver bromoiodide grains with a higher molar proportion of iodide in the core of the grain than in the periphery of the grain, such as those described in GB 1,027,146; JA 54/48,521; U.S. Pat. Nos. 4,379,837; 4,444,877; 4,665,012; 4,686,178; 4,565,778; 4,728,602; 4,668,614; 4,636,461; EP 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsion, i.e., emulsions that form latent images primarily on the surfaces of the silver halide grains, or internal latent image-forming emulsions, i.e., emulsions that form latent images predominantly in the interior of the silver halide grains. The emulsions can be negative-working, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated. Typical chemical sensitizers are listed in *Research Disclosure*, Section III.

The silver halide emulsions can be spectrally sensitized with dyes from a variety of classes, including the polymethine dye class, which includes the cyanines, merocyanines, complex cyanines and merocyanines (i.e., tri-, tetra-, and polynuclear cyanines and merocyanines), oxonols, hemioxonols, styryls, merostyryls, and streptocyanines. Illustrative spectral sensitizing dyes are disclosed in *Research Disclosure*, Section IV.

Suitable vehicles for the emulsion layers and other layers of the recording materials of this invention are described in *Research Disclosure*, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The photographic recording materials of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section X), coating aids (Research Disclosure Section XI), plasticizers and lubricants (Research Disclosure Section XIII), matting agents (Research Disclosure Section XVI and development modifiers (Research Disclosure Section XXI).

The photographic materials can be coated on a variety of supports as described in Research Disclosure Section XVII and the references described therein.

Photographic recording materials can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the recording material with a color developing agent to reduce developable silver halide and oxidize the color developing agent. Oxidized color developing agent in turn reacts with the coupler to yield a dye.

Preferred color developing agents are p-phenylene diamines. Especially preferred are 4-amino-3-methyl-N,N-diethylaniline hydrochloride, 4-amino-3-methyl-N-ethyl-N-β-(methanesulfonamido)-ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxy-ethyl)-m-toluidine di-p-toluene sulfonic acid.

With negative-working silver halide, the processing step described above provides a negative image. The described recording materials are preferably processed in the known C-41 color process as described in, for example, the British Journal of Photography Annual of 1982, pages 209–211. To provide a positive (or reversal) image, the color development step can be preceded by development with a non-chromogenic developing agent to develop exposed silver halide, but not form dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver or silver halide, washing, and drying.

The following examples are included for a further understanding of the invention.

EXAMPLE 1

The invention is illustrated by the following examples. In these examples there was employed the following photographic film structure and composition:

| PHOTOGRAPHIC FILM |
|---|
| Gelatin (1.08 g/m²), |
| Bis (vinylsulfonyl) ether hardener (0.09 g/m²) |
| Chemically sensitized AgBrI (6 mol % I) (1.6 g/m²), Gelatin (2.4 g/m²), Coupler as identified in the tables (1.61 mmole/m²), |
| SUPPORT |

In the following examples each film segment was sensitometrically exposed through a graduated density test object for 3 seconds and then processed using the Kodak C-41 R process as described in the *British Journal of Photography* 1982 Annual, pp. 209–211.

After reading the red dye density (designated $D_i$) in each of the processed elements of a step of the sensitometric curve closest to the density 1.0, each element was further treated for 5 minutes in a continuously-stirred, nitrogen-purged bath having the following composition:

| | |
|---|---|
| Distilled water | 800.0 ml |
| Ethylene diamine tetraacetic acid | 32.1 g |
| Concentrated ammonium hydroxide | 30.0 ml |
| Ferrous sulfate heptahydrate | 27.8 g |
| pH adjusted to 5.0 with NH₄OH | |
| Total volume adjusted to 1 liter with water. | |

After subsequent washing for 5 minutes and final drying, each sample was reevaluated by another density reading (designated $D_f$) of the same step on the sensitometric curve. The percent dye loss recorded in the following table was calculated by dividing the initial density value ($D_i$) into the final density value ($D_f$).

TABLE II

| Coupler Compound | % Dye Density Loss After Treatment in $Fe^{2+}$ |
|---|---|
| I (reference) | 60 |
| II (reference) | 35 |
| A (invention) | 4 |
| B (invention) | 0 |
| C (invention) | 1 |
| D (invention) | 3 |

The data in Table II indicate the coupler compounds of this invention, A to D, greatly reduced dye loss when treated in ferrous ion solution when compared with two well known cyan dye-forming coupler compounds.

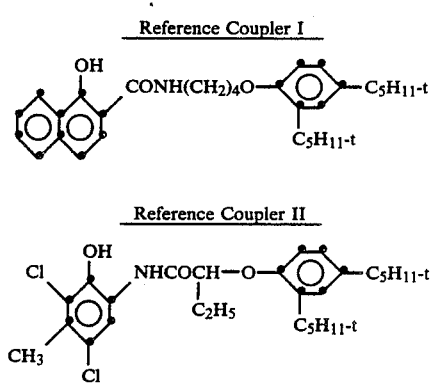

Reference Couplers I and II have long been used commercially in the color photographic art.

This invention has been described in detail with particular reference to preferred embodiments thereof, but it will be understood that variations and modifications can be effected within the spirit and scope of the invention.

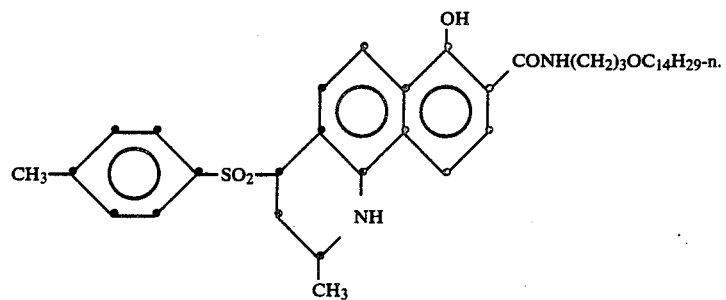

I claim:

1. A photographic recording material comprising a support and a photosensitive silver halide emulsion which has associated therewith a cyan dye-forming coupler having the structural formula:

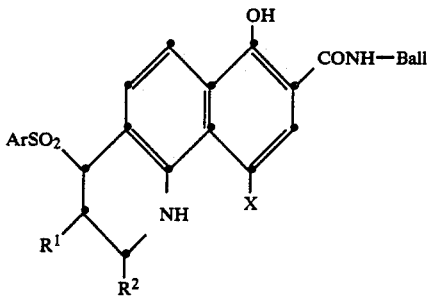

wherein:

Ar is an aryl group having from 6 to 10 carbon atoms which may be substituted;

$R^1$ and $R^2$, which may be the same or different, represent hydrogen or an alkyl group having from 1 to 20 carbon atoms;

Ball is an organic ballasting group capable of rendering the coupler compound non-diffusible during development in alkaline processing solution; and X is hydrogen or a coupling-off group.

2. The recording material of claim 1 wherein Ar is an unsubstituted or a substituted phenyl group.

3. The recording material of claim 2 wherein Ar comprises an alkyl substituent having from 1 to 30 carbon atoms.

4. The recording material of claim 1 wherein $R^1$ and $R^2$ are alkyl groups having from 1 to about 20 carbon atoms.

5. The recording material of claim 1 wherein $R^1$ is hydrogen and $R^2$ is methyl.

6. The recording material of claim 1 wherein X is hydrogen.

7. The recording material of claim 1 wherein the dye-forming coupler has the formula:

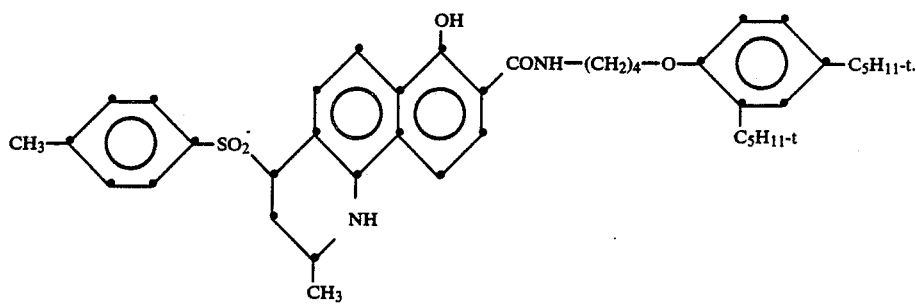

8. The recording material of claim 1 wherein the dye-forming coupler has the formula:

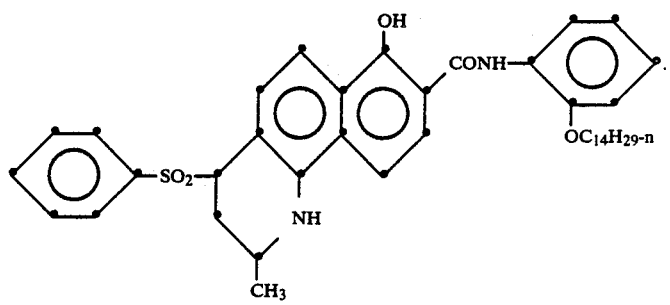

9. The recording material of claim 1 wherein the dye-forming coupler has the formula:

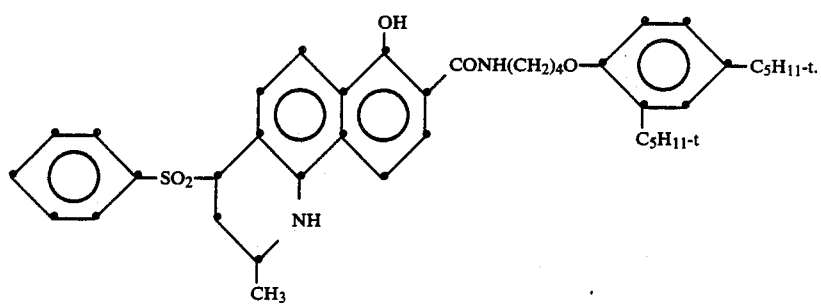

10. The recording material of claim 1 wherein the dye-forming coupler has the formula: